(12) United States Patent
Dairiki et al.

(10) Patent No.: US 8,273,685 B2
(45) Date of Patent: Sep. 25, 2012

(54) AGROCHEMICAL COMPOSITION

(75) Inventors: Hiroshi Dairiki, Odawara (JP); Satoru Yamamura, Makinohara (JP)

(73) Assignee: Nippon Soda Co., Ltd., Tokyo (JP)

( * ) Notice: Subject to any disclaimer, the term of this patent is extended or adjusted under 35 U.S.C. 154(b) by 369 days.

(21) Appl. No.: 12/309,354

(22) PCT Filed: Aug. 8, 2007

(86) PCT No.: PCT/JP2007/065515
§ 371 (c)(1),
(2), (4) Date: Jan. 15, 2009

(87) PCT Pub. No.: WO2008/018501
PCT Pub. Date: Feb. 14, 2008

(65) Prior Publication Data
US 2009/0286682 A1    Nov. 19, 2009

(30) Foreign Application Priority Data

Aug. 10, 2006  (JP) .............................. 2006-217891

(51) Int. Cl.
A01N 59/00 (2006.01)
A01N 43/653 (2006.01)
A01N 43/64 (2006.01)
A61K 31/41 (2006.01)

(52) U.S. Cl. .................. 504/124; 504/273; 514/383
(58) Field of Classification Search .................. 504/124, 504/273; 514/383
See application file for complete search history.

(56) References Cited

U.S. PATENT DOCUMENTS

| 4,973,353 | A | * | 11/1990 | Shida et al. ................... 504/273 |
| 6,664,213 | B1 | | 12/2003 | Furusawa et al. |
| 2001/0014347 | A1 | | 8/2001 | Koike |
| 2002/0042440 | A1 | | 4/2002 | Mizutani et al. |
| 2003/0060367 | A1 | | 3/2003 | Bieringer et al. |
| 2003/0186816 | A1 | | 10/2003 | Hacker et al. |
| 2006/0035787 | A1 | | 2/2006 | Dairiki et al. |
| 2006/0189485 | A1 | | 8/2006 | Hirokawa et al. |

FOREIGN PATENT DOCUMENTS

| JP | A-60-38363 | 2/1985 |
| JP | A-61-72754 | 4/1986 |
| JP | A-8-225413 | 9/1996 |
| JP | A-10-279403 | 10/1998 |
| JP | A-2000-508291 | 7/2000 |
| JP | A-2001-010915 | 1/2001 |
| JP | A-2001-213848 | 8/2001 |
| JP | A-2001-233715 | 8/2001 |
| JP | A-2002-356460 | 12/2002 |
| JP | A-2002-363170 | 12/2002 |
| JP | A-2003-63910 | 3/2003 |
| JP | A-2003-095809 | 4/2003 |
| JP | A-2004-010492 | 1/2004 |
| JP | 2004-168665 A | 6/2004 |
| JP | A-2004-168865 | 6/2004 |
| JP | 2004-217646 A | 8/2004 |
| JP | A-2004-250371 | 9/2004 |
| JP | A-2004-538329 | 12/2004 |
| JP | A-2005-104959 | 4/2005 |
| JP | A-2005-527507 | 9/2005 |
| JP | A-2005-314439 | 11/2005 |
| WO | WO0120984 A1 * | 3/2001 |
| WO | WO 2004/014136 A1 | 2/2004 |

OTHER PUBLICATIONS

STIC Search enclosed (Mar. 24, 2011).*
Office Action dated Jul. 26, 2011, in corresponding Korean Application No. 10-2009-7002393, 4 pages, with English translation, 4 pages.

* cited by examiner

Primary Examiner — Johann Richter
Assistant Examiner — Jane C Oswecki
(74) Attorney, Agent, or Firm — Foley & Lardner LLP

(57) ABSTRACT

An agrochemical composition is provided in which an agrochemically active ingredient having 4 or more fluorine atoms in a molecule and having a Log P value of 3 or more is contained, and superior disintegration dispersibility is exhibited, and which is suitable for a water dispersible granule or a suspension concentrate. An agrochemical composition is characterized by containing (a1) an agrochemically active ingredient having 4 or more fluorine atoms in a molecule and having a Log P value of 3 or more, or (a2) an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds, in an amount ranging from 0.1 to 70% by weight of the total amount of the composition, and (b) a wetting agent such as an alkylsulfate salt, in an amount ranging from 0.1 to 10% by weight of the total amount of the composition.

10 Claims, No Drawings

AGROCHEMICAL COMPOSITION

TECHNOLOGICAL FIELD

The present invention relates to an agrochemical composition containing an agrochemically active ingredient having scanty wettability, and in particular, an agrochemically active ingredient having 4 or more fluorine atoms in a molecule and having a Log P value of 3 or more, or an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds.

The present application claims the priority of Japanese Patent Application No. 2006-217891 filed on Aug. 10, 2006, in Japan, which is hereby incorporated by reference.

BACKGROUND ART

Conventionally, in the field of agrochemicals or the like, it is known that introduction of a fluorine atom into a compound provides preferable results in onsets, enhancements, or improvements in selectivity of pharmacological effects in some cases, and many agrochemically active compounds into which fluorine atoms are introduced are developed.

However, in general, a compound having many fluorine atoms in a molecule or a compound having an increased Log P has water-repellent properties or oil-repellent properties, and exhibits scanty wettability. In particular, a compound having rich water-repellent properties such as a compound having 4 or more fluorine atoms in a molecule and having a Log P value of 3 or more has water-repellent properties or oil-repellent properties, and exhibits scanty wettability. For this reason, it has been difficult to produce agrochemical preparations such as water dispersible granules or suspension concentrates by use of the aforementioned agrochemically active compounds with water-repellent properties and wetting agents.

Therefore, developments have been desired in methods for easily producing agrochemical preparations such as water dispersible granules or suspension concentrates by use of agrochemically active compounds with poor wettabilities as agrochemically technical products.

In connection with the present invention, Patent Document 1 describes an agrochemical granule preparation having an inorganic salt such as potassium chloride, a surfactant such as an alkylsulfate salt, and a product derived from *Bacillus thuringiensis* as an active ingredient. However, the agrochemical granule preparation disclosed in the aforementioned document fails to use an agrochemically active ingredient into which many fluorine atoms are introduced as an active ingredient, and also fails to improve the wettability thereof.

In addition, Patent Document 2 describes a water dispersible granule containing (i) an agrochemically active ingredient in an amount of 0.1 to 60% by weight, (ii) a formaldehyde condensate with an arylsulfonic acid or a salt thereof in an amount of 1 to 20% by weight, (iii) an alkali metal salt or an alkaline earth metal salt of a copolymer having a carboxyl group in an amount of 0.1 to 10% by weight, (iv) a sugar in an amount of 30 to 70% by weight, and (v) an inorganic carrier in an amount of 5 to 30% by weight. As the agrochemically active ingredient (i), a compound having many fluorine atoms in a molecule, such as 5-chloro-6-(1-fluoroethyl)-N-[2-[4-(trifluoromethoxy]phenyl]ethyl]pyrimidin-4-ylamine is used.

However, the water dispersible granule disclosed in the aforementioned document uses 30 to 70% by weight of the sugar as a disintegration additive, and for this reason, in particular, in the case of diluting with water at a low temperature, poor disintegration dispersibility is exhibited, non-uniformity of the active ingredient easily occurs in an aqueous dilution, and non-uniformity during spraying is caused in some cases.

Patent Document 1: Japanese Unexamined Patent Application, First Publication No. 2001-10915
Patent Document 2: Japanese Unexamined Patent Application, First Publication No. 2003-95809

DISCLOSURE OF THE INVENTION

Problems to be Solved by the Invention

The present invention was carried out in view of the circumstances of the aforementioned prior art, and has an objective to provide an agrochemical composition which exhibits superior disintegration dispersibility, and is suitable for a water dispersible granule or a suspension concentrate, by use of an agrochemically active ingredient having 4 or more fluorine atoms in a molecule and having a Log P value of 3 or more, or an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds.

In order to solve the problems described above, the inventors of the present invention carried out diligent studies with respect to an agrochemical composition having, as an active ingredient, (a1) an agrochemically active ingredient having 4 or more fluorine atoms in a molecule and having a Log P value of 3 or more, or (a2) an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds. As a result, it was discovered that by using a specific surfactant as a wetting agent of the aforementioned agrochemical active ingredient, an agrochemical composition exhibiting superior fluidity and disintegration dispersibility can be obtained. In addition, it was discovered that by further adding potassium chloride as a disintegration additive, an agrochemical composition exhibiting superior disintegration dispersibility can be easily produced even in the case of diluting in water at low temperature. The aforementioned discoveries were generalized, and thereby, the present invention was completed.

In accordance with the present invention, agrochemical compositions <1> to <11> described below are provided.

<1> An agrochemical composition characterized by comprising (a1) an agrochemically active ingredient having 4 or more fluorine atoms in a molecule and having a Log P value of 3 or more, in an amount ranging from 0.1 to 70% by weight of the total amount of the composition, and (b) at least one wetting agent selected from the group consisting of alkylsulfate salts, polyoxyalkylene alkyl ethers, alkenylsulfonate salts, polyoxyethylene styryl phenyl ethers, polyoxyethylene distyryl phenyl ethers, polyoxyethylene tristyryl phenyl ethers, polyoxyethylene styryl phenyl ether salts, polyoxyethylene distyryl phenyl ether salts, polyoxyethylene tristyryl phenyl ether salts, and N-acylamino acid salts, in an amount ranging from 0.1 to 10% by weight of the total amount of the composition.

<2> The agrochemical composition according to aforementioned <1>, wherein said agrochemically active ingredient (a1) is a derivative of 1,5-diphenyl-1H-1,2,4-triazole-3-carboxamide represented by formula (1):

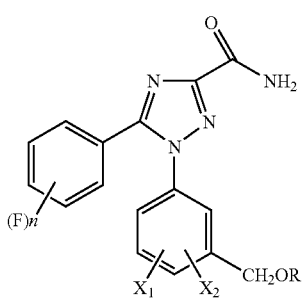

wherein R represents an alkyl group having 1 to 10 carbon atoms optionally substituted by a fluorine atom, a branched alkyl group having 3 to 10 carbon atoms, an alkyl group having 1 to 3 carbon atoms substituted by an alicyclic structure having 3 to 7 carbon atoms, a phenyl group, or an aralkyl group having 7 to 9 carbon atoms; $X_1$ represents a halogen atom or an alkyl group having 1 to 3 carbon atoms; $X_2$ represents a hydrogen atom or a halogen atom; and n represents an integer ranging from 0 to 2.

<3> The agrochemical composition according to the aforementioned <1>, wherein said agrochemically active ingredient (a1) is flupoxam (ISO name: flupoxam, and CAS name: 1-[4-chloro-3-[(2,2,3,3,3-pentafluoropropoxy)methyl]phenyl]-5-phenyl-1H-1,2,4-triazole-3-carboxamide).

<4> An agrochemical composition characterized by comprising (a2) an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds, in an amount ranging from 0.1 to 70% by weight of the total amount of the composition, and (b) at least one wetting agent selected from the group consisting of alkylsulfate salts, polyoxyalkylene alkyl ethers, alkenylsulfonate salts, polyoxyethylene styryl phenyl ethers, polyoxyethylene distyryl phenyl ethers, polyoxyethylene tristyryl phenyl ethers, polyoxyethylene styryl phenyl ether salts, polyoxyethylene distyryl phenyl ether salts, polyoxyethylene tristyryl phenyl ether salts, and N-acylamino acid salts, in an amount ranging from 0.1 to 10% by weight of the total amount of the composition.

<5> The agrochemical composition according to the aforementioned <4>, wherein said agrochemically active ingredient (a2) is a derivative of 1,5-diphenyl-1H-1,2,4-triazole-3-carboxamide represented by formula (1):

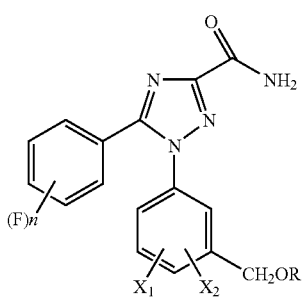

wherein R represents an alkyl group having 1 to 10 carbon atoms optionally substituted by a fluorine atom, a branched alkyl group having 3 to 10 carbon atoms, an alkyl group having 1 to 3 carbon atoms substituted by an alicyclic structure having 3 to 7 carbon atoms, a phenyl group, or an aralkyl group having 7 to 9 carbon atoms; $X_1$ represents a halogen atom or an alkyl group having 1 to 3 carbon atoms; $X_2$ represents a hydrogen atom or a halogen atom; and n represents an integer ranging from 0 to 2.

<6> The agrochemical composition according to the aforementioned <4>, wherein said agrochemically active ingredient (a2) is flupoxam (ISO name: flupoxam, and CAS name: 1-[4-chloro-3-[(2,2,3,3,3-pentafluoropropoxy)methyl]phenyl]-5-phenyl-1H-1,2,4-triazole-3-carboxamide).

<7> The agrochemical composition according to any one of the aforementioned <1> to <6>, further comprising (c) an alkali metal halide in an amount ranging from 1 to 40% by weight of the total amount of the composition, and (d) a powder carrier in an amount ranging from 10 to 40% by weight of the total amount of the composition.

<8> The agrochemical composition according to the aforementioned <7>, wherein said alkali metal halide (c) is potassium chloride or sodium chloride.

<9> The agrochemical composition according to the aforementioned <7> or <8>, wherein said powder carrier (d) is at least one carrier selected from the group consisting of calcium carbonate, calcium sulfate, and diatomaceous earth.

<10> The agrochemical composition according to any one of the aforementioned <7> to <9>, further comprising (e) at least one compound selected from the group consisting of arylsulfonic-acid formaldehyde condensates, arylsulfonate formaldehyde condensates, and salts of copolymers having carboxyl groups in an amount ranging from 1 to 20% by weight of the total amount of the composition.

<11> The agrochemical composition according to any one of the aforementioned <1> to <10>, which is a water dispersible granule or a suspension concentrate.

Effects of the Invention

In accordance with the present invention, an agrochemical composition suitable for a water dispersible granule can be provided, in which the composition comprises (a1) an agrochemically active ingredient having 4 or more fluorine atoms in a molecule and having a Log P value of 3 or more, or (a2) an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds.

The agrochemical compositions of the present invention can be easily produced, and exhibit superior fluidity and superior disintegration dispersibility.

The agrochemical compositions of the present invention exhibit superior disintegration dispersibility, in particular, even in the case of diluting with water at a low temperature (5° C.), and for this reason, they are suitable for water dispersible granules and suspension concentrates.

BEST MODES FOR CARRYING OUT THE INVENTION

The present invention is described in detail below.

The present invention provides an agrochemical composition characterized by comprising (a1) an agrochemically active ingredient having 4 or more fluorine atoms in a molecule and having a Log P value of 3 or more, or (a2) an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds, in an amount ranging from 0.1 to 70% by weight of the total amount of the composition, and (b) at least one wetting agent selected from the group consisting of alkylsulfate salts, polyoxyalkylene alkyl ethers, alkenylsulfonate salts, polyoxyethylene styryl phenyl ethers, polyoxyethylene distyryl phenyl ethers, polyoxyethylene tristyryl phenyl ethers, polyoxyethylene styryl phenyl ether salts, polyoxyethylene distyryl phenyl ether salts, polyoxyethylene tristyryl phenyl ether salts, and N-acyl-amino acid salts, in an amount ranging from 0.1 to 10% by weight of the total amount of the composition.

(a) Agrochemically Active Ingredient

The agrochemically active ingredient (hereinafter, referred to as "agrochemically active ingredient (a)" in some cases) used in the present invention is (a1) an agrochemically active ingredient having 4 or more fluorine atoms in a molecule and having a Log P value of 3 or more (hereinafter, referred to as "agrochemically active ingredient (a1)" in some cases), or (a2) an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds (hereinafter, referred to as "agrochemically active ingredient (a2)" in some cases).

In the present invention, the agrochemically active ingredient means not only agrochemically active ingredient (a1) or agrochemically active ingredient (a2), but also a compound having physiological activities such as herbicidal activities, control activities with respect to pests of agricultural and horticultural products, plant growth regulators, and the like.

In addition, the present invention provides an agrochemical composition exhibiting superior fluidity and superior disintegration dispersibility, by using an agrochemically active ingredient having scanty wettability as an agrochemical product by virtue of water-repellent properties or oil-repellent properties thereof.

(a1) Agrochemically Active Ingredient

The agrochemically active ingredient (a1) used in the present invention is a compound which has agrochemical activities, has 4 or more fluorine atoms and preferably 5 or more fluorine atoms in a molecule, and has a Log P value of 3 or more.

Here, the Log P is a logarithmic value of a 1-octanol/water partition coefficient in a compound, and means an index indicating a lipophilic property of a chemical substance. The greater the Log P value, the higher the lipophilic properties.

As examples of agrochemically active ingredient (a1) used in the present invention, mention may be made of compounds (1) to (14) described below. Needless to say, agrochemically active ingredients (a1) used in the present invention are not limited to the compounds below.

(1) Acrinathrin (ISO name: acrinathrin, IUPAC name: (S)-alpha-cyano-3-phenoxybenzyl (Z)-(1R,3S)-2,2-dimethyl-3-[2-(2,2,2-trifluoro-1-trifluoromethylethoxycarbonyl)vinyl] cyclopropanecarboxylate, Log P=5.25), (2) Diflufenican (ISO name: diflufenican, IUPAC name: 2',4'-difluoro-2-(alpha,alpha,alpha-trifluoro-m-tolyloxy) nicotinanilide, Log P=4.9), (3) Fipronil (ISO name: fipronil, IUPAC name: (+)-5-amino-1-(2,6-dichloro-alpha,alpha,alpha-trifluoro-p-tolyl)-4-trifluoromethylsulfinylpyrazole-3-carbonitrile, Log P=4), (4) Fluazuron (ISO name: fluazuron, IUPAC name: 1-[4-chloro-3-(3-chloro-5-trifluoromethyl-2-pyridyloxy)phenyl]-3-(2,6-difluorobenzoyl)urea, Log P=5.1), (5) Flufenoxuron (ISO name: flufenoxuron, IUPAC name: 1-[4-(2-chloro-alpha,alpha,alpha-trifluoro-p-tolyloxy)-2-fluorophenyl]-3-(2,6-difluorobenzoyl)urea Log P=4.01), (6) Flumetralin (ISO name: flumetralin, IUPAC name: N-(2-chloro-6-fluorobenzyl)-N-ethyl-alpha,alpha,alpha-trifluoro-2,6-dinitro-p-toluidine, Log P>3), (7) Hexaflumuron (ISO name: hexaflumuron, IUPAC name: 1-[3,5-dichloro-4-(1,1,2,2-tetrafluoroethoxy)phenyl]-3-(2,6-difluorobenzoyl)urea, Log P=4.68), (8) Lufenuron (ISO name: lufenuron, IUPAC name: (RS)-1-[2,5-dichloro-4-(1,1,2,3,3,3-hexafluoroprpyl)phenyl]-3-(2,6-difluorobenzoyl)urea Log P=5.12), (9) Sulfluramid (ISO name: sulfluramid, IUPAC name: N-ethylperfluorooctane-1-sulfonamide, Log P>6.85),

(10) Teflubenzuron (ISO name: teflubenzuron, IUPAC name: 1-(3,5-dichloro-2,4-difluorophenyl)-3-(2,6-difluorobenzoyl)urea, Log P>4.3,

(11) Tefluthrin (ISO name: tefluthrin, IUPAC name: 2,3,5, 6-tetrafluoro-4-methylbenzyl (1RS,3RS)-3-[(Z)-2-chloro-3, 3,3-trifluoroprop-1-enyl]-2,2-dimethylcyclopropanecarboxylat Log P=6.5),

(12) Tetraconazole (ISO name: tetraconazole, IUPAC name: (RS)-2-(2,4-dichlorophenyl)-3-(1H-1,2,4-triazol-1-yl)propyl 1,1,2,2-tetrafluoroethyl ether Log P=3.53),

(13) Thiazopyr (ISO name: thiazopyr, IUPAC name: methyl 2-difluoromethyl-5-(4,5-dihydro-1,3-triazol-2-yl)-4-isobutyl-6-trifluoromethylnicotinate, Log P=3.89),

(14) Transfluthrin, (ISO name: transfluthrin, IUPAC name=2,3,5,6-tetrafluorobenzyl (1R,3S)-3-(2,2-dichlorovinyl)-2,2-dimethylcyclopropanecarboxylate, Log P=5.46), and the like.

As preferable examples of the aforementioned compounds, mention may be made of 1,5-diphenyl-1H-1,2,4-triazole-3-carboxamide derivatives. Among these, flupoxam (ISO name: flupoxam, CAS name: 1-[4-chloro-3-[(2,2,3,3,3-pentafluoropropoxy)methyl]phenyl]-5-phenyl-1H-1,2,4-triazole-3-carboxamide) is particularly preferable.

(a2) Agrochemically Active Ingredient

Agrochemically active ingredient (a2) used in the present invention is a compound for which, in a fluidity test of a mixture composed of 50 parts by weight of the agrochemically active ingredient, 2 parts by weight of sorbitan monooleate and 48 parts by weight of water, the time for moving 85 mm is not less than 90 seconds.

The fluidity test is a test for verifying whether or not a material is a liquid product specified under Article 69$^{bis}$ in "Rules related regulations of hazardous materials" in Japan. More particularly, in this test, a mixture composed of 50 parts by weight of the agrochemically active ingredient, 2 parts by weight of sorbitan monooleate and 48 parts by weight of water is placed in a test tube (a test tube formed from glass, having a flat-bottomed cylindrical shape with an inner diameter of 30 mm and a height of 120 mm) (hereinafter referred to as "test tube") vertically set until the amount of the mixture is at 55 mm of the height from the bottom of the test tube, and when the aforementioned test tube is horizontally set, the time elapsed until the leading end of the moving surface of the aforementioned product passes through the position of 85 mm from the bottom of the test tube is measured.

As examples of agrochemically active ingredient (a2), mention may be made of:

fungicides such as TPN, azoxystrobin, isoprothiolane, iprodione, iminoctadine albesilate, iminoctadine triacetate, imibenconazole, echlomezole, oxycarboxin, captan, kresoxim-methyl, chloroneb, cyproconazole, simeconazole, wettable sulfur, thiuram, thiophanate-methyl, thifluzamide, tetraconazole, tebuconazole, triadimefon, triclofos methyl, triflumizole, triforine, tolclofos-methyl, validamycin, validamycin A, bitertanol, hydroxyisoxazole, pyributicarb, fenarimol, ferimzone, flutolanil, procymidone, propamocarb hydrochloride, propiconazole, benomyl, pencycuron, fosetyl-Al, polyoxin, polyoxin D, polyoxin D zinc salt, polycarbamate, myclobutanil, metalaxyl, mepronil, oxine copper, and the like;

insecticides such as BT, CVMP, CVP, CYAP, DDVP, DEP, MEP, MIPC, NAC, PHC, acetamiprid, acephate, isoxathion, imidacloprid, ethofenprox, clothianidin, chlorpyrifos, cyhalothrin, silafluofen, *Steinernema glaseri*, *Steinernema carpocapsae*, spinosad, diazinon, thiamethoxam, thiodicarb, tebufenozide, teflubenzuron, tralomethrin, bifenthrin, pyridafenthion, fenobucarb, bulwelure•lawculture, prothiofos, permethrin microcapsule, permethrin, bensultap, methomyl, monocrotophos, acrinathrin, fipronil, fluazuron, flufenoxuron, hexaflumuron, lufenuron, sulfuramide, teflubenzuron, tefluthrin, transfluthrin, and the like, herbicides such as 2,4-PA, CAT, MCPP, MCP, isopropylamine salt, MDBA, SAP, asulam, amiprofos-methyl, alachlor, isoxaben, imazaquin ammonium, imazosulfuron, ethoxysulfuron, endothal disodium salt, oxadiargyl, oxaziclomefone, orizalin, orthobencarb, cafenstrole, *Xanthomonas campestris* pv. *poas*, cyanazine, cyclosulfamron, dithiopyr, siduron, cinosulfuron, cinmethylin, thenylchlor, triaziflam, triclopyr, trifloxysulfuron sodium salt, napropamide, halosulfuron methyl, pyrifenox, pyributicarb, butamifos, flazasulfuron, prodiamine, propyzamide, florasulam, bethrodine, pendimethalin, mecoprop P calcium salt, methyldaimuron, metsulfuron-methyl, lenacil, diflufenican, thiazopyr, and the like;

plant growth regulators such as flumethralin, and the like; and the like.

The aforementioned agrochemically active ingredients (a) composed of the aforementioned agrochemically active ingredients (a1) or agrochemically active ingredients (a2) can be used alone or in combination with two or more types thereof. In the case of using a combination with two or more types thereof, the blending ratio thereof can be freely selected. In addition, when the agrochemically active ingredients (a) used have a plurality of optical isomers, geometrical isomers and the like, the aforementioned isomers may be used alone or two or more types thereof may be used in combination.

The blending amount of the aforementioned agrochemically active ingredient (a) ranges from 0.1 to 70% by weight with respect to the total amount of the composition, and preferably ranges from 10 to 60% by weight.

In the agrochemical compositions of the present invention, in addition to the aforementioned agrochemically active ingredients (a), agrochemically active ingredients other than these can be further contained. By using the aforementioned agrochemically active ingredients (a) together with the other agrochemically active ingredients, additional effects or remarkable synergetic effects may be obtained in some cases.

The other agrochemically active ingredients are not particularly limited, may be in the form of a liquid or solid, may be organic compounds or inorganic compounds, and may be a single compound or a mixture.

As examples of other agrochemically active ingredients, mention may be made of fungicides, insecticides, herbicides, and the like, described below.

Fungicides:
TPN, azoxystrobin, isoprothiolane, iprodione, iminoctadine albesilate, iminoctadine triacetate, imibenconazole, echlomezole, oxycarboxin, captan, kresoxim-methyl, chloroneb, cyproconazole, simeconazole, wettable sulfur, thiuram, thiophanate-methyl, thifluzamide, tetraconazole, tebuconazole, triadimefon, triclofos methyl, triflumizole, triforine, tolclofos-methyl, validamycin, validamycin A, bitertanol, hydroxyisoxazole, pyributicarb, fenarimol, ferimzone, flutolanil, procymidone, propamocarb hydrochloride, propiconazole, benomyl, pencycuron, fosetyl-Al, polyoxin, polyoxin D, polyoxin D zinc salt, polycarbamate, myclobutanil, metalaxyl, mepronil, oxine copper, and the like.

Insecticides:
BT, CVMP, CVP, CYAP, DDVP, DEP, MEP, MIPC, NAC, PHC, acetamiprid, acephate, isoxathion, imidacloprid, ethofenprox, clothianidin, chlorpyrifos, cyhalothrin, silafluofen, *Steinernema glaseri*, *Steinernema carpocapsae*, spinosad, diazinon, thiamethoxam, thiodicarb, tebufenozide, teflubenzuron, tralomethrin, bifenthrin, pyridafenthion, fenobucarb, bulwelure•lawculture, prothiofos, permethrin microcapsule, permethrin, bensultap, methomyl, monocrotophos, acrinathrin, fipronil, fluazuron, flufenoxuron, hexaflumuron, lufenuron, sulfuramide, teflubenzuron, tefluthrin, transfluthrin, and the like.

Herbicides:
2,4-PA, CAT, MCPP, MCP, isopropylamine salt, MDBA, SAP, asulam, amiprofos-methyl, alachlor, isoxaben, imazaquin ammonium, imazosulfuron, ethoxysulfuron, endothal disodium salt, oxadiargyl, oxaziclomefone, orizalin, orthobencarb, cafenstrole, *Xanthomonas campestris* pv. *poas*, cyanazine, cyclosulfamron, dithiopyr, siduron, cinosulfuron, cinmethylin, thenylchlor, triaziflam, triclopyr, trifloxysulfuron sodium salt, napropamide, halosulfuron methyl, pyrifenox, pyributicarb, butamifos, flazasulfuron, prodiamine, propyzamide, florasulam, bethrodine, pendimethalin, mecoprop P calcium salt, methyldaimuron, metsulfuron-methyl, lenacil, diflufenican, thiazopyr, and the like.

Plant Growth Regulators:
flumethralin, and the like.

The blending amount of the aforementioned other agrochemically active ingredient is determined so that the total amount of the aforementioned agrochemically active ingredient (a) and the aforementioned other agrochemically active ingredient ranges from 0.1 to 70% by weight with respect to the total amount of the composition, and preferably ranges from 10 to 60% by weight.

In the agrochemical compositions of the present invention, additive components can be further blended. By using the aforementioned agrochemically active ingredients (a) or using the aforementioned agrochemically active ingredients (a) and other agrochemically active ingredients, together with the aforementioned additive components, additional effects or remarkable synergetic effects may be obtained in some cases.

The additive components are not particularly limited, may be in the form of a liquid or solid, may be organic compounds or inorganic compounds, and may be a single compound or a mixture.

More particularly, synergists, antidotes, agents for decreasing phytotoxicity, antibacterial agents, antifungal agents, and anti-algae agents can be mentioned.

Synergists, antidotes, and agents for decreasing phytotoxicity:
Octachlorodipropyl ether, piperonyl butoxide, cyneprin, IBTA, benoxacor, cloquintocet-methyl, ciometranil, dichlormid, fenchlorazole-ethyl, fencloram, flurazole, flaxofenimi, furilazole, mefenpyr-diethyl, MG191, naphthalic anhydride, oxabetrinil, and the like.

Antibacterial Agents, Antifungal Agents, and Anti-Algae Agents:

Trialkyltriamine, ethanol, isopropyl alcohol, propyl alcohol, trisnitro, chlorobutanol, pronopol, glutaraldehyde, formaldehyde, alpha-bromcinnamaldehyde, scane M-8, caisson CG, NS-500W, BIT, n-butyl BIT, allyl isothiocyanate, thiobendazole, methyl 2-benzimidazolyl carbamate, lauricidine, biovan, triclocarban, halocarban, glasisicar, benzoic acid, sorbic acid, caprylic acid, propionic acid, 10-undecylenic acid, potassium sorbate, potassium propionate, potassium benzoate, monomagnesium phthalate, zinc undecylenate, 8-hydroxyquinoline, copper quinoline, TMTD, triclosan, diclohelanilide, tolyfluanid, milt protein, egg white lysozyme, benthiazole, sodium carbam, triazine, tebuconazole, hinokithiol, tetrachloroisophthalonitrile, tectamer 38, chlorhexidine gluconate, chlorhexidine hydrochloride, polyhexamethylene biguanide, polybiguanide hydrochloride, danthoprom, clidant, sodium pyrithion, zinc pyrithion, densil, copper pyrithion, thymol, isopropyl methyl phenol, OPP, phenol, butyl paraben, ethyl paraben, methyl paraben, propyl paraben, metacresol, orthocresol, paracresol, sodium orthophenyl phenol, chlorofen, parachlorophenol, parachloromethaxylate, parachlorocresol, fluorfolpet, polylysine, biopan P-1487, Jote methylparatolylsulfone, polyvinylpyrrolidone parachloroisocyanel, hydrogen peroxide, stabilized chlorine dioxide, peracetic acid, copper naphthenate, novalon AG 300, silver chloride, titanium oxide, silver, zinc-calcium phosphate, Silver Ace, silver-zinc aluminosilicate, silver-zinc zeolite, novalon AGZ 330, phorone killer, dimmer 136, benzalkonium chloride, didecyl dimethyl ammonium chloride, bardack 2250/80, benzotonium chloride, high-amy 3500J, cetylammonium bromide, Cetrimide, CTAB, Cetavlon, Dimer-38, benzalkonium chloride, BARDAC® 170P, DC-5700, cetyl pyridinium chloride, chitosan, deuron, DCMU, prepentol A6, CMI, 2CI-OIT, BCM, ZPT, BNP, OIT, IPBC, TCMSP, and the like.

The aforementioned additive components can be used alone or by mixing two or more types thereof.

(b) Wetting Agent

The agrochemical composition of the present invention contains a wetting agent in an amount ranging from 0.1 to 10% by weight with respect to the total amount of the composition.

The wetting agent has a role for wetting the aforementioned agrochemically active ingredient (a) and imparting superior disintegration dispersibilities to the agrochemical composition.

The wetting agent used in the present invention is at least one compound selected from the group consisting of alkylsulfate salts, polyoxyalkylene alkyl ethers, alkenylsulfonate salts, polyoxyethylene styryl phenyl ethers, polyoxyethylene distyryl phenyl ethers, polyoxyethylene tristyryl phenyl ethers, polyoxyethylene styryl phenyl ether salts, polyoxyethylene distyryl phenyl ether salts, polyoxyethylene tristyryl phenyl ether salts, and N-acylamino acid salts.

Here, as examples of alkyl ethers of polyoxyalkylenes, mention may be made of $R\text{-}(EO)_x$, $R\text{—}O\text{-}(PO)_y$, ethers of polyoxyethylenes and copolymers of polyoxyethylenes. As examples of copolymers, mention may be made of $R\text{—}O\text{-}(EO)_x\text{-}(PO)_y$, $R\text{—}O\text{-}(PO)_y\text{-}(EO)_x$, $R\text{—}O\text{-}(EO)_x\text{-}(PO)_y\text{-}(EO)_z$, $R\text{—}O\text{-}(EO)_z\text{-}(PO)_y\text{-}(EO)_x$, and the like, wherein EO: ethylene oxy group,
PO: propylene oxy group,
R: alkyl group,
x: a number ranging from 1 to 30 on average,
y: a number ranging from 1 to 30 on average, and
z: a number ranging from 1 to 30 on average.

In addition, the polyoxyethylene group moiety used in the present invention has a degree of polymerization ranging from 2 to 50, and preferably has a degree of polymerization ranging from 4 to 40.

In addition, as examples of polyoxyethylene styryl phenyl ether salts, polyoxyethylene distyryl phenyl ether salts, and polyoxyethylene tristyryl phenyl ether salts, mention may be made of formaldehyde condensates, sulfate salts, and phosphate salts.

As examples of cations of the aforementioned salts, mention may be made of salts of an alkali metal such as potassium, sodium, or the like, salts of an alkaline earth metal such as calcium, magnesium, or the like, and alkanolamine salts such as mono-, di-, or triethanolamine salts.

In addition, as examples of N-acyl groups of N-acylamino acid salts, mention may be made of higher fatty acid acyl groups having 6 to 24 carbon atoms such as a coconut oil fatty acid acyl group, a stearoyl group, or the like. As example of amino acids of N-acylamino acid salts, mention may be made of L-amino acids such as L-glutamic acid and the like. As examples of salts of N-acylamino acid salts, mention may be made of alkali metal salts such as sodium salt, potassium salt, and the like; alkaline earth metal salts such as magnesium, salt, calcium salt, and the like; and the like. As preferable examples thereof, mention may be made of sodium N-coconut oil fatty acid acyl-L-glutamate, and disodium N-stearoyl-L-glutamate.

Among these, as the wetting agent used in the present invention, in the case of producing a water dispersible granule, an alkylsulfate salt or a polyoxyethylene tristyryl phenyl ether sulfate salt is preferably used, and the alkylsulfate salt is, in particular, preferably used.

The blending amount of the aforementioned wetting agent usually ranges from 0.1 to 10% by weight with respect to the amount of the agrochemical composition of the present invention, and preferably ranges from 0.5 to 5% by weight.

In the agrochemical composition of the present invention, preferably, (c) an alkali metal halide and (d) a powder carrier are further contained.

(c) Alkali Metal Halide

An alkali metal halide used in the present invention is an inorganic salt which can be dissolved in an amount of not less than 0.1 g in 100 g of water at 5° C. of water temperature. As examples thereof, mention may be made of fluorides, chlorides, bromides, and the like of an alkali metal such as sodium, potassium, or the like. The aforementioned alkali metal halides can be used alone or in combination with two or more types thereof. Among these, potassium chloride or sodium chloride is, in particular, preferable. Sodium chloride or potassium chloride provides good disintegrabilities in water when a water dispersible granule is produced. In view of this, sodium chloride or potassium chloride which is pulverized into microparticles having a particle size ranging from 10 to 500 μm is preferably used.

The blending amount of the aforementioned alkali metal halide (c) usually ranges from 1 to 40% by weight with respect to the total amount of the composition, and preferably ranges from 5 to 20% by weight.

(d) Powder Carrier

As examples of powder carriers used in the present invention, mention may be made of diatomaceous earth, kaolin clay, acid clay, talc, calcium carbonate, calcium sulfate, Attapulgite clay, and the like. The aforementioned powder carriers can be used alone or in combination with two or more types thereof. Among these, diatomaceous earth, calcium carbonate, and calcium sulfate are preferable, and diatomaceous earth is, in particular, preferable.

The blending amount of the aforementioned powder carrier (d) usually ranges from 10 to 50% by weight with respect to the total amount of the composition, and preferably ranges from 10 to 40% by weight.

In the present invention, water dispersible granules having good disintegrability in water at 5° C. to room temperature can be produced. Preferably, water dispersible granules having a good disintegrability in water at 5° C. to 20° C. can be produced. In order to produce the aforementioned water dispersible granules, both alkali metal halides (c) and powder carriers (d) are preferably contained in the agrochemical compositions of the present invention. In addition, the mixing ratio (weight ratio) of alkali metal halides (c) and powder carriers (d) preferably ranges from 1:1 to 1:15.

(e) Dispersant

In the agrochemical composition of the present invention, as a dispersant, at least one compound (e) is selected from the group consisting of arylsulfonic-acid formaldehyde condensates, arylsulfonate formaldehyde condensates, and salts of copolymers having carboxyl groups. By means of using the aforementioned compounds, even if the agrochemically active ingredients having water repellency are used, water dispersible granules having good disintegrability of granules in water at room temperature or low temperature can be produced.

As examples of formaldehyde condensates with arylsulfonic acids, mention may be made of, for example, a formaldehyde condensate with phenylsulfonic acid, a formaldehyde condensate with tolylphenylsulfonic acid, a formaldehyde condensate with naphthylphenylsulfonic acid, a formaldehyde condensate with an alkylnaphthalenesulfonic acid, a formaldehyde condensate with naphthalenesulfonic acid, a formaldehyde condensate with a specific aromatic sulfonic acid, and the like. They may be a mixture of two or more types thereof.

As examples of salts of formaldehyde condensates with arylsulfonic acids, mention may be made of formaldehyde condensates with sodium, calcium or potassium salts of the aforementioned arylsulfonic acids. In addition, they may be a mixture of a formaldehyde condensate with an arylsulfonic acid and a salt of a formaldehyde condensate with an arylsulfonic acid, in any mixing ratio.

As examples of salts of copolymers having carboxyl groups, mention may be made of, for example, a sodium salt of a copolymer between maleic acid and diisobutylene, a calcium salt of the aforementioned copolymer, a sodium salt of a copolymer between maleic acid and isobutylene, a calcium salt of the aforementioned copolymer, a sodium salt of a copolymer between acrylic acid and itaconic acid, a calcium salt of the aforementioned copolymer, a sodium salt of a copolymer between maleic acid and styrene, a calcium salt of the aforementioned copolymer, and the like.

The total amount of the formaldehyde condensates with arylsulfonic acids or salts thereof and salts of copolymers having carboxyl groups usually ranges from 0.1 to 70% by weight with respect to the total amount of the composition, preferably ranges from 1 to 40% by weight, and more preferably ranges from 3 to 20% by weight.

As described below, when the agrochemical composition of the present invention is a water dispersible granule or a suspension concentrate, a viscous binder or a thickener may be contained in the agrochemical composition.

The usable viscous binders or thickeners are not particularly limited. As examples thereof, mention may be made of, for example, starch, dextrin, cellulose, methylcellulose, ethylcellulose, carboxymethylcellulose, hydroxyethylcellulose, hydroxypropylcellulose, carboxymethyl starch, pullulan, sodium alginate, ammonium alginate, propylene glycol alginate, guar gum, locust bean gum, Arabic gum, xanthan gum, gelatin, casein, polyvinyl alcohol, polyethylene oxide, polyethylene glycol, a block polymer of ethylene and propylene, sodium polyacrylate, polyvinylpyrrolidone, carageenan, and the like.

The viscous binders or thickeners can be used alone or in combination with two or more types thereof.

The blending amount of the viscous binders or thickeners is not particularly limited. In view of effects obtained by the addition thereof and economic properties, the amount thereof preferably ranges from 0.1 to 40 parts by weight with respect to 100 parts by weight of the composition.

In the agrochemical composition of the present invention, a surfactant can be further blended within a range which does not impair the effects of the present invention.

The usable surfactants are not particularly limited as long as they are materials other than those listed as examples used as the aforementioned wetting agents. As examples thereof, mention may be made of conventional nonionic surfactants, anionic surfactants, cationic surfactants, amphoteric surfactants, and combinations thereof.

The agrochemical composition of the present invention may further contain additive components in addition to the ingredients described above. The usable additive components are not particularly limited. As examples thereof, mention may be made of, for example, the aforementioned synergists, antidotes, agents for decreasing phytotoxicity, antibacterial agents, antifungal agents, and anti-algae agents, as well as, preservatives, solvents, antioxidants, UV absorbents, agents for preventing crystallization, and the like.

In addition, the agrochemical composition of the present invention may contain solid or liquid additive components such as stabilizers, examples of which include epoxylated or non-epoxylated vegetable oils (such as epoxylated coconut oil, rapeseed oil, or soybean oil), antifoaming agents (such as silicone oil), viscosity adjustors, binders and/or adhesives, as well as, other effective ingredients such as germicides, fungicides, bactericides, insecticides, or mitecides.

Among these, the agrochemical composition of the present invention is preferably in the form of a water dispersible granule or a suspension concentrate. The water dispersible granule or suspension concentrate preferably contains the aforementioned agrochemically active ingredient (a) in an amount of 0.1 to 70% by weight with respect to the total amount of the composition, and the aforementioned wetting agent (b) in an amount of 0.1 to 10% by weight with respect to the total amount of the composition, and optionally contains an alkali metal halide (c) in an amount of 1 to 40% by weight with respect to the total amount of the composition, a powder carrier (d) in an amount of 10 to 40% by weight with respect to the total amount of the composition, and at least one type (e) selected from the group consisting of formaldehyde condensates with arylsulfonic acids, salts of formaldehyde condensates with arylsulfonic acids, and salts of copolymers having carboxyl groups in an amount of 1 to 20% by weight with respect to the total amount of the composition. In particular, the water dispersible granule preferably contains the aforementioned agrochemically active ingredient (a) in an amount of 0.1 to 70% by weight with respect to the total amount of the composition, and the aforementioned wetting agent (b) in an amount of 0.1 to 10% by weight with respect to the total amount of the composition, and optionally contains an alkali metal halide (c) in an amount of 1 to 40% by weight with respect to the total amount of the composition, a powder carrier (d) in an amount of 10 to 40% by weight with respect to the total amount of the composition, and at least one type (e) selected from the group consisting of formaldehyde condensates with arylsulfonic acids, salts of formaldehyde condensates with arylsulfonic acid, and salts of copolymers having carboxyl groups in an amount of 1 to 20% by weight with respect to the total amount of the composition.

The agrochemical composition of the present invention which is a water dispersible granule exhibits a good disintegrability at a water temperature of 20° C. and 5° C. Even if a dilute solution is prepared at high altitudes or in a cold region, in the period in which water is cold in the season from winter to spring, the granules do not remain in the preparation, and non-uniformity of active ingredients in the dilute solution may be prevented.

The agrochemical composition of the present invention exhibits superior fluidity. In the agrochemical composition of the present invention, preferably, in a fluidity test immediately after mixing, the time for moving 85 mm is less than 90 seconds. In addition, more preferably, even in a fluidity test 24 hours after mixing, the time for moving 85 mm is less than 90 seconds.

Here, the fluidity test is the test described above.

The agrochemical compositions of the present invention can be produced into various agrochemical formulations in accordance with a known method.

For example, a water dispersible granule can be produced by adding water to a wettable powder, kneading the mixture, extruding the kneaded mixture, and drying it to make granules.

A wettable powder can be produced by pulverizing a mixture by means of a jet mill such as Ulmax (manufactured by Nisso Engineering Co., Ltd.).

A suspension concentrate can be produced by mixing an agrochemically active ingredient with a surfactant, a thickening agent, a preservative, an anti-foaming agent, and the like, and pulverizing the mixture by means of a wet pulverizer which is charged with beads.

An emulsifiable concentrate can be produced by dissolving an agrochemically active ingredient and a surfactant in an organic solvent.

An oil-in-water emulsion can be produced by adding a solution obtained by dissolving an agrochemically active ingredient and a surfactant in an organic solvent to water to homogenize the mixture, or gradually adding water to a solution obtained by dissolving an agrochemically active ingredient and a surfactant in an organic solvent to homogenize the mixture.

In addition, a suspoemulsion can be produced by stirring an oil-in-water emulsion and a suspension concentrate by means of a three-one motor or the like.

The formulated agrochemical compositions of the present invention are diluted with water or the like and then applied to plants, at the water level or to soils. In addition, they can also be used together with other fungicides, herbicides, insecticides, fertilizers, soil conditioners, and the like.

The amount of application of the agrochemical composition of the present invention usually ranges from 1 to 1,000 g as the amount of the agrochemically active ingredient per hectare, and preferably ranges from 10 to 500 g.

EXAMPLES

Hereinafter, the present invention is described in detail with reference to Examples and Comparative Examples. It should be understood that the present invention is not limited to the Examples described below. All "parts" described below mean "parts by weight".

Examples 1 to 17 and Comparative Examples 1 to 18

Agrochemical compositions according to Examples 1 to 17 and Comparative Examples 1 to 18 were prepared by mixing 50 parts of flupoxam (1-[4-chloro-3-[(2,2,3,3,3-pentafluoropropoxy)methyl]phenyl]-5-phenyl-1H-1,2,4-triazole-3-carboxamide), 2 parts of the wetting agent shown in Table 1 and Table 2 described below, and 48 parts of water.

The wetting agents shown in Table 1 and Table 2 are those described below.

POE means polyoxyethylene, POA means polyoxyalkylene, and POP means polyoxypropylene.

(b-1): sodium laurylsulfate (product name: NEWKALGEN LX-C, manufactured by Takemoto Oil & Fat Co., Ltd.)

(b-2): alpha-olefin sulfonate/phosphate blended product (product name: SORPOL 5160, manufactured by Toho Chemical Industry Co., Ltd.)

(b-3): alpha-olefin sulfonate (product name: SORPOL 5115, manufactured by Toho Chemical Industry Co., Ltd.)

(b-4): POE (17) tristyryl phenyl ether phosphate (product name: SORPOL 7777, manufactured by Toho Chemical Industry Co., Ltd.)

(b-5): POE (14) tristyryl phenyl ether sulfate/silica blended product (product name: SORPOL 5096, manufactured by Toho Chemical Industry Co., Ltd.)

(b-6): POE (14) tristyryl phenyl ether (product name: SORPOL T-15, manufactured by Toho Chemical Industry Co., Ltd.)

(b-7): POE (19) tristyryl phenyl ether (product name: SORPOL T-20, manufactured by Toho Chemical Industry Co., Ltd.)

(b-8): POE (24) tristyryl phenyl ether (product name: SORPOL T-26, manufactured by Toho Chemical Industry Co., Ltd.)

(b-9): POE (30) tristyryl phenyl ether (product name: SORPOL T-32, manufactured by Toho Chemical Industry Co., Ltd.)

(b-10): POE (21) distyryl phenyl ether formaldehyde condensate (product name: SORPOL F-15, manufactured by Toho Chemical Industry Co., Ltd.)

(b-11): POE (26) distyryl phenyl ether formaldehyde condensate (product name: SORPOL F-18, manufactured by Toho Chemical Industry Co., Ltd.)

(b-12): POE (34) distyryl phenyl ether formaldehyde condensate (product name: SORPOL F-24, manufactured by Toho Chemical Industry Co., Ltd.)

(b-13): POE (38) distyryl phenyl ether formaldehyde condensate (product name: SORPOL F-27, manufactured by Toho Chemical Industry Co., Ltd.)

(b-14): POA alkyl ether (HLB 13.4, product name: Emulgen LS-110, manufactured by Kao Corporation)

(b-15): POA alkyl ether (HLB 14.0, product name: Emulgen LS-114, manufactured by Kao Corporation)

(b-16): sodium N-stearoyl-L-glutamate (product name: AMISOFT HS-11, manufactured by Ajinomoto Co., Inc.)

(b-17): sodium N-coconut oil fatty acid acyl-L-glutamate (product name: AMISOFT CS-11, manufactured by Ajinomoto Co., Inc.)

(b-18): sorbitan monooleate (product name: NEWKALGEN D-935, manufactured by Takemoto Oil & Fat Co., Ltd.)

(b-19): metal salt of polycarboxylic acid (product name: NEWKALGEN WG-5, manufactured by Takemoto Oil & Fat Co., Ltd.)

(b-20): sodium alkylnaphthalenesulfonate (product name: NEWKALGEN BX-C, manufactured by Takemoto Oil & Fat Co., Ltd.)

(b-21): sodium dodecylbenzenesulfonate (product name: NEWKALGEN SX-C, manufactured by Takemoto Oil & Fat Co., Ltd.)

(b-22): sodium naphthalene sulfonate formaldehyde condensate (product name: NEWKALGEN PS-P, manufactured by Takemoto Oil & Fat Co., Ltd.)

(b-23): ammonium POE allyl phenyl ether sulfate (product name: NEWKALGEN NX-6529, manufactured by Takemoto Oil & Fat Co., Ltd.)

(b-24): sodium dioctylsulfosuccinate (product name: NEWKALGEN EX-70, manufactured by Takemoto Oil & Fat Co., Ltd.)

(b-25): POE fatty acid ester (product name: NEWKALGEN NV-2420, manufactured by Takemoto Oil & Fat Co., Ltd.)

(b-26): sodium phenol sulfonate formaldehyde condensate (product name: NEWKALGEN TX-C, manufactured by Takemoto Oil & Fat Co., Ltd.)

(b-27): POP-POE block copolymer (POE 80%) (product name: PLURONIC PE 6800, manufactured by BASF)

(b-28): POP-POE block copolymer (POE 50%) (product name: PLURONIC PE 10500, manufactured by BASF)

(b-29): POE sorbitan monooleate (product name: NEWKALGEN D-945, manufactured by Takemoto Oil & Fat Co., Ltd.)

(b-30): POE castor oil ether (product name: NEWKALGEN D-212, manufactured by Takemoto Oil & Fat Co., Ltd.)

(b-31): POE hydrogenated castor oil ether (product name: NEWKALGEN D-225K, manufactured by Takemoto Oil & Fat Co., Ltd.)

(b-32): POE stearyl ether (product name: EMULGEN 320P, manufactured by Kao Corporation)

(b-33): POE oleyl ether (product name: EMULGEN 420, manufactured by Kao Corporation)

(b-34): silicon-based surfactant (product name: SILWET 408, manufactured by GE Toshiba Silicones Co., Ltd.)

(b-35): POE alkyl (C16-18) ether (product name: Newcol-1606, manufactured by Nippon Nyukazai Co., Ltd.)

Fluidity Test

Each of the aforementioned agrochemical compositions prepared in Examples 1 to 17 and Comparative Examples 1 to 18 was placed in a test tube (a test tube formed from glass, having a flat-bottomed cylindrical shape with an inner diameter of 30 mm and a height of 120 mm) (hereinafter referred to as "test tube") vertically set until the amount of the composition was at 55 mm of the height from the bottom of the test tube. Immediately after and 24 hours after the entire composition was uniformly mixed, when the aforementioned test tube was horizontally set, the time (hereinafter, referred to as "T") elapsed until the leading end of the moving surface of the aforementioned agrochemical composition passed through the height of 85 mm from the bottom of the test tube was measured.

As a result of the measurements, in the case of T being less than 90 seconds both immediately after and 24 hours after the composition was mixed, the evaluation was ○ (which corresponds to the case in which fluidity was exhibited even if the composition was stored for a long time); in the case of T being less than 90 seconds immediately after the composition was mixed, but T being not less than 90 seconds 24 hours after the composition was mixed, the evaluation was Δ (which corresponds to the case in which fluidity was exhibited immediately after the composition was mixed, but fluidity lost (the composition was solidified) over the time); and in the case of T being not less than 90 seconds immediately after the composition was mixed, the evaluation was X (which corresponds to the case in which fluidity was not exhibited or the agrochemically active compound was not wet).

The evaluation results are shown in Table 1 and Table 2.

TABLE 1

|  | Wetting agent | Evaluation |
|---|---|---|
| Example 1 | b-1 | ○ |
| Example 2 | b-2 | ○ |
| Example 3 | b-3 | ○ |
| Example 4 | b-4 | ○ |
| Example 5 | b-5 | ○ |
| Example 6 | b-6 | ○ |
| Example 7 | b-7 | ○ |
| Example 8 | b-8 | ○ |
| Example 9 | b-9 | ○ |
| Example 10 | b-10 | ○ |
| Example 11 | b-11 | ○ |
| Example 12 | b-12 | ○ |
| Example 13 | b-13 | ○ |
| Example 14 | b-14 | ○ |
| Example 15 | b-15 | ○ |
| Example 16 | b-16 | ○ |
| Example 17 | b-17 | ○ |

TABLE 2

|  | Wetting agent | Evaluation |
|---|---|---|
| Comparative Example 1 | b-18 | X |
| Comparative Example 2 | b-19 | X |
| Comparative Example 3 | b-20 | X |
| Comparative Example 4 | b-21 | X |
| Comparative Example 5 | b-22 | X |
| Comparative Example 6 | b-23 | Δ |
| Comparative Example 7 | b-24 | Δ |
| Comparative Example 8 | b-25 | Δ |
| Comparative Example 9 | b-26 | X |
| Comparative Example 10 | b-27 | Δ |
| Comparative Example 11 | b-28 | Δ |
| Comparative Example 12 | b-29 | X |
| Comparative Example 13 | b-30 | X |
| Comparative Example 14 | b-31 | X |
| Comparative Example 15 | b-32 | Δ |
| Comparative Example 16 | b-33 | Δ |
| Comparative Example 17 | b-34 | X |
| Comparative Example 18 | b-35 | Δ |

Example 18

An agrochemical composition of Example 18 was prepared by mixing 50 parts of thiophanate-methyl, 2 parts of POE(14) tristyryl phenyl ether (product name: SORPOL T-15, manufactured by Toho Chemical Industry Co., Ltd.), and 48 parts of water.

Example 19

An agrochemical composition of Example 19 was prepared by mixing 50 parts of diflufenican, 2 parts of POE(14) tristyryl phenyl ether (product name: SORPOL T-15, manufactured by Toho Chemical Industry Co., Ltd.), and 48 parts of water.

Comparative Example 19

An agrochemical composition of Comparative Example 19 was prepared by mixing 50 parts of thiophanate-methyl, 2 parts of sorbitan monooleate (product name: NEWKALGEN D-935, manufactured by manufactured by Takemoto Oil & Fat Co., Ltd.), and 48 parts of water.

Comparative Example 20

An agrochemical composition of Comparative Example 20 was prepared by mixing 50 parts of diflufenican, 2 parts of sorbitan monooleate (product name: NEWKALGEN D-935, manufactured by manufactured by Takemoto Oil & Fat Co., Ltd.), and 48 parts of water.

Fluidity Test

Each of the aforementioned agrochemical compositions prepared in Examples 18 and 19 and Comparative Examples 19 and 20 was subjected to the same fluidity test as described above.

As a result of the measurements, both immediately after and 24 hours after the composition was mixed, in Examples 18 and 19, T was less than 90 seconds, and fluidity could be exhibited even if the composition was stored for a long time.

On the other hand, in the compositions of Comparative Examples 19 and 20, immediately after the composition was mixed, T was 90 or more seconds, and fluidity was not exhibited.

Examples 20 to 25 and Comparative Examples 21 to 30

Water dispersible granules of Examples 20 to 25 and Comparative Examples 21 to 30 were prepared by mixing (a) the agrochemically active ingredient, (b) the wetting agent, (c) the water-soluble inorganic salt (alkali metal halide), (d) the powder carrier, and optionally (e) the surfactant (arylsulfonic-acid formaldehyde condensate, arylsulfonate formaldehyde condensate, and salt of copolymer having carboxyl group) described below in the ratio shown in Table 3 and Table 4; pulverizing the obtained mixture by means of a hammer mill; adding 45 parts of water thereto; kneading the mixture; extrusion-granulating the kneaded mixture with a 0.7 mm screen; drying granules for 24 hours at 70° C.; sieving the granules with 0.59 mm and 0.84 mm sieve; and batching off the parts remaining on a 0.59 mm to 0.84 mm sieve to obtain water dispersible granules.

(a) Agrochemically Active Ingredient:

Flupoxam (1-[4-chloro-3-[(2,2,3,3,3-pentafluoropropoxy)methyl]phenyl]-5-phenyl-1H-1,2,4-triazole-3-carboxamide).

(b) Wetting Agent:

A: sodium laurylsulfate (product name: NEWKALGEN LX-C, manufactured by Takemoto Oil & Fat Co., Ltd.)

B: sodium alkylnaphthalenesulfonate (produce name: NEWKALGEN BX-C, manufactured by Takemoto Oil & Fat Co., Ltd.)

(c) Water-Soluble Inorganic Salt (Alkali Metal Halide):

A: potassium chloride

B: Ammonium sulfate

C: potassium dihydrogenphosphate (d) Powder Carrier:

A: diatomaceous earth (product name: KUNILITE 201, manufactured by Kunimine Industries Co., Ltd.)

B: calcium carbonate

C: lactose (product name: DMV Lactose #200, manufactured by DMV Company)

D: kaolin (product name: KAOLIN NSW, manufactured by Kanaya Kousan Corp.)

(e) Surfactant (Arylsulfonic-Acid Formaldehyde Condensate, Arylsulfonate Formaldehyde Condensate, or Salt of Copolymer Having Carboxyl Group):

A: sodium naphthalene sulfonate formaldehyde condensate (product name: NEWKALGEN PS-P, manufactured by Takemoto Oil & Fat Co., Ltd.)

B: metal salt of polycarboxylic acid (product name: NEWKALGEN WG-5, manufactured by Takemoto Oil & Fat Co., Ltd.) C: sodium lignin sulfonate (product name: NEWKALGEN RX-B, Takemoto Oil & Fat Co., Ltd.)

TABLE 3

| Ingredients of composition | | Example 20 | Example 21 | Example 22 | Example 23 | Example 24 | Example 25 |
|---|---|---|---|---|---|---|---|
| Agrochemically active ingredient | A | 50.6 | 50.6 | 50.6 | 50.6 | 50.6 | 50.6 |
| Wetting agent | A | 1.0 | 1.0 | 1.0 | 1.0 | 1.0 | 1.0 |
| | B | | | | | | |
| Water-soluble inorganic salt | A | 10.0 | 5.0 | 2.5 | 10.0 | 10.0 | 10.0 |
| | B | | | | | | |
| | C | | | | | | |
| Powder carrier | A | 27.4 | 32.4 | 34.9 | | 23.4 | 32.4 |
| | B | | | | 27.4 | | |
| | C | | | | | | |
| | D | | | | | | |
| Surfactant | A | 6.0 | 6.0 | 6.0 | 6.0 | 8.0 | 4.0 |
| | B | 5.0 | 5.0 | 5.0 | 5.0 | 7.0 | 2.0 |
| | C | | | | | | |

TABLE 4

| Ingredients of composition | | Comparative Example 21 | Comparative Example 22 | Comparative Example 23 | Comparative Example 24 | Comparative Example 25 | Comparative Example 26 | Comparative Example 27 | Comparative Example 28 | Comparative Example 29 | Comparative Example 30 |
|---|---|---|---|---|---|---|---|---|---|---|---|
| Agrochemically active ingredient | A | 50.6 | 50.6 | 50.6 | 50.6 | 50.6 | 50.6 | 50.6 | 50.6 | 50.6 | 50.6 |
| Wetting agent | A | 1.0 | 1.0 | 1.0 | 1.0 | 1.0 | 1.0 | 1.0 | 1.0 | 1.0 | |
| | B | | | | | | | | | | 2.0 |
| Water-soluble inorganic salt | A | 37.4 | | 10.0 | | 10.0 | | | 5.0 | 10.0 | 10.0 |
| | B | | | | | | 10.0 | | | | |
| | C | | | | | | | 10.0 | | | |
| Powder carrier | A | | 37.4 | | | | 27.4 | 27.4 | 35.4 | 29.4 | 29.4 |
| | B | | | | | | | | | | |
| | C | | | 27.4 | 37.4 | | | | | | |
| | D | | | | | 27.4 | | | | | |
| Surfactant | A | 6.0 | 6.0 | 6.0 | 6.0 | 6.0 | 4.0 | | | 4.0 | 6.0 |
| | B | 5.0 | 5.0 | 5.0 | 5.0 | 5.0 | 2.0 | | 2.0 | | 5.0 |
| | C | | | | | | | | 6.0 | 5.0 | |

Test Example 1

Disintegration dispersibility test of water dispersible granules using water at 20° C. and 5° C.

The tests described below were carried out on water dispersible granules of Examples 20 to 25 and Comparative Examples 21 to 30.

(1) Evaluation Test of Self Dispersibility

A Nessler tube was charged with 100 ml of 53.6 ppm hard water, and 100 mg of the water dispersible granule was added from the edge of the tube and was allowed to stand. The condition in which the water dispersible granule was naturally dispersed therein was observed, and evaluation was carried out on the basis of the evaluation criteria described below.

○: case in which disintegration started above half the height of the Nessler tube.

Δ: case in which disintegration started below half the height of the Nessler tube.

X: case in which disintegration did not occur at all.

The evaluation results are shown in Table 5.

(2) Measurement of the Number of Times of Turnover to Disintegration

An agrochemical formulation having preferable disintegration dispersibility had a number of times of turnover until the water dispersible granule was disintegrated in water at water temperature of 5° C. of at most 10 times, and had a number of times of turnover until the water dispersible granule was disintegrated in water at water temperature of 20° C. of at most 5 times.

The measurement results are shown in Table 5.

It can be seen from Table 5 that the water dispersible granules of Examples 20 to 25 exhibited superior disintegration dispersibility even in the case of using water at 5° C.

On the other hand, the water dispersible granule of Comparative Example 21 in which the contained amount of potassium chloride (alkali metal halide) was increased, the water dispersible granule of Comparative Example 22 which included no alkali metal halide, and the water dispersible granule of Comparative Example 25 which included Kaolin NSW in addition to the alkali metal halide, exhibited poor disintegrability.

The water dispersible granule of Comparative Example 23 which included DMV lactose in addition to the alkali metal halide, and the water dispersible granule of Comparative Example 24 which included DMV lactose instead of the alkali metal halide, exhibited poor disintegrability, in particular, in the case of using water at low temperature (5° C.).

The water dispersible granule of Comparative Example 26 in which ammonium sulfate was used instead of the alkali metal halide, and the water dispersible granule of Comparative Example 27 in which sodium dihydrogen phosphate was used instead of the alkali metal halide, exhibited remarkably inferior disintegrability and self dispersibility to those of Examples.

The water dispersible granule of Comparative Example 28 in which a metal salt of a polycarboxylic acid (surfactant B) and sodium lignin sulfonate (surfactant C) were used instead of the sodium naphthalene sulfonate formaldehyde condensate (surfactant A) used in the Examples, and the water dispersible granule of Comparative Example 29 in which sodium lignin sulfonate (surfactant C) was used instead of the

TABLE 5

| | Water temperature: 20° C. | | Water temperature: 5° C. | |
|---|---|---|---|---|
| | Self dispersiblity | Number of times of turnover to disintegration (times) | Self dispersiblity | Number of times of turnover to disintegration (times) |
| Example 20 | ○ | 3 | ○ | 7 |
| Example 21 | ○ | 4 | ○ | 8 |
| Example 22 | ○ | 5 | ○ | 7 |
| Example 23 | Δ | 5 | Δ | 9 |
| Example 24 | ○ | 4 | ○ | 9 |
| Example 25 | ○ | 4 | ○ | 8 |
| Comparative Example 21 | ○ | 7 | Δ | 14 |
| Comparative Example 22 | Δ | 10 | Δ | 11 |
| Comparative Example 23 | ○ | 8 | Δ | 13 |
| Comparative Example 24 | ○ | 9 | Δ | 12 |
| Comparative Example 25 | Δ | 19 | Δ | 20 |
| Comparative Example 26 | X | >30 | X | >30 |
| Comparative Example 27 | X | 16 | X | 19 |
| Comparative Example 28 | Δ | 5 | X | 20 |
| Comparative Example 29 | Δ | 5 | Δ | 13 |
| Comparative Example 30 | X | >30 | X | >30 | metal salt of the polycarboxylic acid (surfactant B) used in the Examples, exhibited inferior self dispersibility, compared to the Examples.

In addition, the water dispersible granule of Comparative Example 30 in which wetting agent B (sodium alkylnaphthalene sulfonate) was used instead of wetting agent A exhibited inferior self dispersibility and inferior disintegrability, compared to the Examples.

Example 26

20 parts of polyoxyethylene (14 mol) tristyryl phenyl ether, 0.5 parts of dioctyl sulfosuccinate, 0.5 parts of a silicon-based antifoaming agent (product name: Antifoam SE 39, manufactured by Wacker Asahikasei Silicone Co., Ltd.), 0.1 parts of 1,2-benzisothiazoline-containing preparation (product name: PROXEL GXL(s), manufactured by Avecia Limited), and 35.8 parts of water were added to 25.8 parts of flupoxam (1-[4-chloro-3-[(2,2,3,3,3-pentafluoropropoxy)methyl]phenyl]-5-phenyl-1H-1,2,4-triazole-3-carboxamide), followed by mixing.

The obtained mixture was subjected to wet milling under the conditions described below by means of a planetary mill (P-7 model, manufactured by FRITSCH GmbH), and thereby, a wet pulverized product was obtained.

Conditions of Wet Milling
Glass beads used: 1.6 to 2.0 mm (High beads D-11) 5 ml
Number of rotations: 800 rpm
Milling time: 15 minutes A solution obtained by dissolving 5.0 parts of propylene glycol, and 0.3 parts of xanthan gum (product name: Rhodopol 23, manufactured by Rohne-Poulenc Inc.) in 30 parts of water was mixed with the aforementioned wet milled product. Thereby, a suspended form composition (suspension concentrate) (1) was obtained.

Comparative Example 31

A suspended form composition (suspension concentrate) (2) was obtained in the same manner as described in Example 26, with the exception of replacing 2.0 parts of polyoxyethylene (14 mol) tristyryl phenyl ether in Example 26 with 2.0 parts of POP-POE block copolymer (POE 80%) (product name: PLURONIC PE6800, manufactured by BASF GmbH).

The same fluidity test as described above was carried out using the suspended form compositions (1) and (2) prepared in Example 26 and Comparative Example 31, respectively, and evaluation was carried out in the same manner as described above.

As a result of the tests and evaluations, in the aforementioned suspended form composition (1), T was less than 90 seconds immediately after and 24 hours after the mixing step. On the other hand, in the aforementioned suspended form composition (2), T was less than 90 seconds immediately after the mixing step, but T was not less than 90 seconds 24 hours after the mixing step.

INDUSTRIAL APPLICABILITY

In accordance with the present invention, an agrochemical composition is provided, which is suitable for a water dispersible granule containing an agrochemically active ingredient with scanty wettability which has 4 or more fluorine atoms in a molecule and has a Log P value of 3 or more, or containing an agrochemically active ingredient for which, in a fluidity test of a mixture composed of 50 parts by weight of the agrochemically active ingredient, 2 parts by weight of sorbitan monooleate and 48 parts by weight of water, the time for moving 85 mm is not less than 90 seconds.

The agrochemical composition of the present invention is easily produced, and exhibits superior fluidity and superior disintegration dispersibility.

The agrochemical composition of the present invention exhibits superior disintegration dispersibility even in the case of diluting with water, in particular, at low temperature (5° C.), and the agrochemical composition is suitable for a water dispersible granule and a suspension concentrate.

The invention claimed is:
1. An agrochemical composition comprising:
(a) an agrochemically active ingredient (a1) having 4 or more fluorine atoms in a molecule and having a Log P value of 3 or more, in an amount ranging from 0.1 to 70% by weight of the total amount of the composition,
(b) at least one wetting agent selected from the group consisting of alkylsulfate salts, polyoxyalkylene alkyl ethers, alkenylsulfonate salts, polyoxyethylene styryl phenyl ethers, polyoxyethylene distyryl phenyl ethers, polyoxyethylene tristyryl phenyl ethers, polyoxyethylene styryl phenyl ether salts, polyoxyethylene distyryl phenyl ether salts, polyoxyethylene tristyryl phenyl ether salts, and N-acylamino acid salts, in an amount ranging from 0.1 to 10% by weight of the total amount of the composition,
(c) an alkali metal halide selected from the group consisting of potassium chloride and sodium chloride, in an amount ranging from 1 to 40% by weight of the total amount of the composition, and
(d) at least one powder carrier selected from the group consisting of calcium carbonate, calcium sulfate, and diatomaceous earth in an amount ranging from 10 to 40% by weight of the total amount of the composition,
wherein a mixing weight ratio of said (c) alkali metal halide and said (d) powder carrier ranges from 1:1 to 1:15.
2. The agrochemical composition according to claim 1, wherein said agrochemically active ingredient (a1) is a derivative of 1,5-diphenyl-1H-1,2,4-triazole-3-carboxamide represented by formula (1):

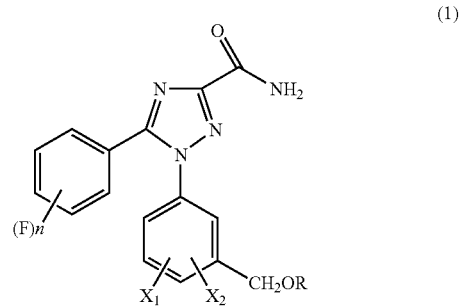

wherein:
R represents:
an alkyl group having 1 to 10 carbon atoms,
a fluorine-substituted alkyl group having 1 to 10 carbon atoms,
a branched alkyl group having 3 to 10 carbon atoms,
an alkyl group having 1 to 3 carbon atoms substituted by an alicyclic structure having 3 to 7 carbon atoms,
a phenyl group, or
an aralkyl group having 7 to 9 carbon atoms;

$X_1$ represents a halogen atom or an alkyl group having 1 to 3 carbon atoms;

$X_2$ represents a hydrogen atom or a halogen atom; and n represents an integer ranging from 0 to 2.

3. The agrochemical composition according to claim 1, wherein said agrochemically active ingredient (a1) is flupoxam (ISO name: flupoxam, and CAS name: 1-[4-chloro-3-[(2,2,3,3,3-pentafluoropropoxy)methyl]phenyl]-5-phenyl-1H-1,2,4-triazole-3-carboxamide).

4. An agrochemical composition comprising:
   (a) an agrochemically active ingredient (a2) for which, in a fluidity test of a mixture composed of:
       50 parts by weight of the agrochemically active ingredient,
       2 parts by weight of sorbitan monooleate, and
       48 parts by weight of water,
   the time for moving 85 mm is not less than 90 seconds, in an amount ranging from 0.1 to 70% by weight of the total amount of the composition,
   (b) at least one wetting agent selected from the group consisting of alkylsulfates, polyoxyalkylene alkyl ethers, alkenylsulfonates, polyoxyethylene styryl phenyl ethers, polyoxyethylene distyryl phenyl ethers, polyoxyethylene tristyryl phenyl ethers, polyoxyethylene styryl phenyl ether salts, polyoxyethylene distyryl phenyl ether salts, polyoxyethylene tristyryl phenyl ether salts, and N-acylamino acid salts, in an amount ranging from 0.1 to 10% by weight of the total amount of the composition,
   (c) an alkali metal halide selected from the group consisting of potassium chloride and sodium chloride, in an amount ranging from 1 to 40% by weight of the total amount of the composition, and
   (d) at least one powder carrier selected from the group consisting of calcium carbonate, calcium sulfate, and diatomaceous earth in an amount ranging from 10 to 40% by weight of the total amount of the composition,
   wherein a mixing weight ratio of said (c) alkali metal halide and said (d) powder carrier ranges from 1:1 to 1:15.

5. The agrochemical composition according to claim 4, wherein said agrochemically active ingredient (a2) is a derivative of 1,5-diphenyl-1H-1,2,4-triazole-3-carboxamide represented by formula (1):

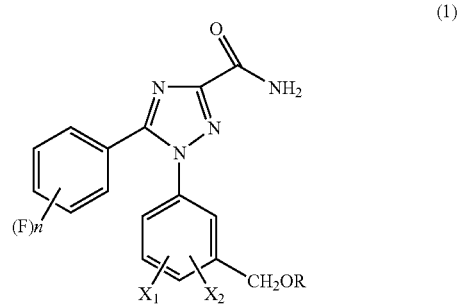

wherein
   R represents
       an alkyl group having 1 to 10 carbon atoms,
       a fluorine-substituted alkyl group having 1 to 10 carbon atoms,
       a branched alkyl group having 3 to 10 carbon atoms,
       an alkyl group having 1 to 3 carbon atoms substituted by an alicyclic structure having 3 to 7 carbon atoms,
       a phenyl group, or
       an aralkyl group having 7 to 9 carbon atoms;
   $X_1$ represents a halogen atom or an alkyl group having 1 to 3 carbon atoms;
   $X_2$ represents a hydrogen atom or a halogen atom; and
   n represents an integer ranging from 0 to 2.

6. The agrochemical composition according to claim 4, wherein said agrochemically active ingredient (a2) is flupoxam (ISO name: flupoxam, and CAS name: 1-[4-chloro-3-[(2,2,3,3,3-pentafluoropropoxy)methyl]phenyl]-5-phenyl-1H-1,2,4-triazole-3-carboxamide).

7. The agrochemical composition according to claim 1, further comprising:
   (e) at least one compound selected from the group consisting of arylsulfonic-acid formaldehyde condensates, arylsulfonate formaldehyde condensates, and salts of copolymers having carboxyl groups in an amount ranging from 1 to 20% by weight of the total amount of the composition, wherein said salts of copolymers having carboxyl groups are selected from the group consisting of sodium and calcium salts of:
       a copolymer between maleic acid and diisobutylene,
       a copolymer between maleic acid and isobutylene,
       a copolymer between acrylic acid and itaconic acid, and
       a copolymer between maleic acid and styrene.

8. The agrochemical composition according to claim 1, which is a water dispersible granule or a suspension concentrate.

9. The agrochemical composition according to claim 4, further comprising:
   (e) at least one compound selected from the group consisting of arylsulfonic-acid formaldehyde condensates, arylsulfonate formaldehyde condensates, and salts of copolymers having carboxyl groups in an amount ranging from 1 to 20% by weight of the total amount of the composition, wherein said salts of copolymers having carboxyl groups are selected from the group consisting of sodium and calcium salts of:
       a copolymer between maleic acid and diisobutylene,
       a copolymer between maleic acid and isobutylene,
       a copolymer between acrylic acid and itaconic acid, and
       a copolymer between maleic acid and styrene.

10. The agrochemical composition according to claim 4, which is a water dispersible granule or a suspension concentrate.

* * * * *